United States Patent [19]

Quadro

[11] Patent Number: 5,352,703
[45] Date of Patent: Oct. 4, 1994

[54] ANTITUSSIVE AND MUCUS REGULATING AGENT, A PROCESS FOR THE PREPARATION THEREOF AND PHARMACEUTICAL COMPOSITIONS CONTAINING IT

[75] Inventor: Giuseppe Quadro, Milan, Italy

[73] Assignee: Mediolanum Farmaceutici S.p.A., Milan, Italy

[21] Appl. No.: 952,838

[22] PCT Filed: Jun. 3, 1991

[86] PCT No.: PCT/EP91/01023
§ 371 Date: Nov. 23, 1993
§ 102(e) Date: Nov. 23, 1992

[87] PCT Pub. No.: WO91/18865
PCT Pub. Date: Dec. 12, 1991

[30] Foreign Application Priority Data

Jun. 6, 1990 [IT] Italy ................. 20562 A/90

[51] Int. Cl.$^5$ ............... A61K 31/165; C07C 233/66
[52] U.S. Cl. ............... 514/617; 514/849; 514/850; 564/184; 564/183; 564/182
[58] Field of Search ............... 564/184, 161, 182, 183; 514/617, 849, 850

[56] References Cited

U.S. PATENT DOCUMENTS 4,191,780  3/1980  Tosi ..................... 514/617

FOREIGN PATENT DOCUMENTS 0004026  9/1979  European Pat. Off. .
0061157  9/1982  European Pat. Off. .
0150787  8/1985  European Pat. Off. .
 01023  12/1991  European Pat. Off. .
2440596  1/1975  Fed. Rep. of Germany .
2835043  12/1979  Fed. Rep. of Germany .

*Primary Examiner*—Shailendra Kumar
*Attorney, Agent, or Firm*—Bucknam and Archer

[57] ABSTRACT

2-benzoylamino-3,5-dibromo-N-(4-hydroxycyclohexyl)benzylamine of formula (I), and pharmaceutically acceptable acid addition salts have antitussive and mucus regulating activities.

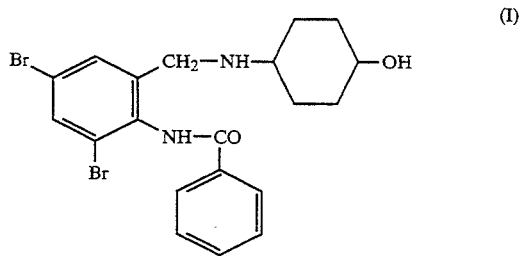

4 Claims, No Drawings

ANTITUSSIVE AND MUCUS REGULATING AGENT, A PROCESS FOR THE PREPARATION THEREOF AND PHARMACEUTICAL COMPOSITIONS CONTAINING IT

The present invention relates to 2-benzoylamino-3,5-dibromo-N-(4-hydroxycyclohexyl)benzylamine of formula (I)

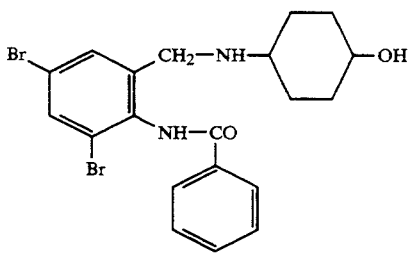

and to the salts thereof with pharmaceutically acceptable acids.

A particularly preferred salt is the hydrochloride salt, which has been used for the pharmacological tests and will be named hereinafter YS 912.

2-Amino-3,5-dibromo-N-(4-hydroxycyclohexyl)benzylamine is a known medicament which has been used for a long time in human therapy. The compound of the present invention is an Ambroxol benzoyl derivative, having improved pharmacological and pharmacokinetic features in comparison with the parent compound.

Compound (I) or a salt thereof (for example YS 912), for the envisaged therapeutic uses as an antitussive and/or mucus regulating agent, will suitably be formulated, according to conventional techniques and excipients, in pharmaceutical compositions for the oral, parenteral or rectal administrations, such as capsules, tablets, syrups, granulates, vials or ampoules, suppositories.

The amount of the active ingredient will depend on a number of factors, such as weight and age of the patient and severity of the disease to be treated, but generally it will range from 5 to 100 mg daily, in one or more administrations. The compositions of the present invention are particularly suited for the treatment of bronchitis, tracheobronchitis, emphysema, sinusitis, otitis, pneumonia of both acute and chronic nature.

Compound (I) is prepared by reacting a benzoic acid reactive derivative (chloride, mixed anhydride, imidazolide etc.) with Ambroxol in suitable solvents and using appropriate reaction conditions.

In fact, acylation also takes place on the secondary amine group, which is more basic: however, the resulting acylated product can rearrange to compound (I) by treatment with HCl gas under heating. The chloride is particularly preferred as the benzoic acid reactive derivative: in this instance the reaction is preferably carried out in the presence of pyridine.

The obtained compound is then treated with HCl gas at a temperature ranging from 30° to 70° C. in a solvent such as ethanol or acetone.

The following Example further illustrates the present invention.

EXAMPLE

Benzoyl chloride (9.2 ml, 0.079 mole) is added to a solution of 3,5-dibromo-N-(4'-cyclohexanol)benzylamine (30 g, 0.079 mole) in toluene (150 ml). Pyridine (6.5 ml, 0.079 mole) is dropped therein, keeping temperature below 20° C. The reaction mixture is left at room temperature for 3 hours, then is washed with 150 ml of water. The organic phase is dried over MgSO$_4$, then evaporated to obtain a residue which is crystallized from ethanol, then dissolved in acetone and added with HCl-saturated acetone to acid pH. The mixture is left at room temperature for 2 hours, then the resulting solid is filtered and washed with acetone.

m.p. 278°–280° C.

NMR (90 MHz; DM50-D$_2$O): δ 1.7, 1.8, 2.7, 3.8, 4.5, 7.1, 7.5.

Pharmacological tests.

ANTITUSSIVE ACTIVITY

1. Citric acid induced cough in Guinea pig.

The procedure described by R.A. Turner in "Screening methods in pharmacology-Antitussive agents" -Academic Press. New York-chapt. 23-page 219, 1965, with the changes reported by S. Malandrino et al. (Arzneim. Forsch. Drug. REs, 38, 1141, 1988), was used, comparing YS 912 with Ambroxol.

The results are reported in the following Table I, from which a remarkable antitussive activity is evidenced for YS 912, said activity being higher than that of Ambroxol, at the different used doses.

| | | | Cough strokes | | % |
|---|---|---|---|---|---|
| Treatment | Dose mg/kg ip. | Body weight (g) | Basal | After treatment | inhibition vs. basal |
| Controls | — | 265.60 ± 11.38 | 7.90 ± 1.31 | 7.10 ± 1.12 | 10.13 |
| AMBROXOL | 12.5 | 270.00 ± 12.11 | 9.20 ± 1.41 | 7.40 ± 1.32 | 19.57 |
| | 25 | 275.10 ± 10.69 | 9.60 ± 1.28 | 6.20 ± 0.61 | 35.42 |
| | 50 | 280.00 ± 10.04 | 8.90 ± 1.02 | 4.80 ± 1.02 | 46.07 |
| YS 912 | 12.5 | 279.30 ± 10.98 | 7.70 ± 1.15 | 2.90 ± 0.60 | 62.34 |
| | 25 | 283.60 ± 9.20 | 9.20 ± 1.15 | 2.30 ± 0.54 | 75.00 |
| | 50 | 285.40 ± 9.60 | 9.50 ± 1.41 | 2.00 ± 0.47 | 78.95 |

Antitussive activity-Citric acid cough in Guinea pig. Means ± S. E. of cough strokes before and after treatment (n = 10).

The effective dose 50 (ED$_{50}$) evidences the higher potency of YS 912, which is 14 times higher than that of Ambroxol:

| DE$_{50}$: | Ambroxol | = 57.18 mg/kg |
|---|---|---|
| | YS-912 | = 4.81 mg/kg |

2. NH$_3$ induced cough in Guinea pig.

The procedure described by R. A. Turner in "Screening methods in pharmacology-Antitussive agents" -Academic Press. New York-chapt. 23-page 219, 1965 with the changes reported by S. Malandrino et al. (Arzneim. Forsch. Drug. Res, 38, 1141, 1988) was used, comparing YS 912, Ambroxol and two standard control drugs: Fominoben and Codeine phosphate. The results are reported in the following Table 2.

| Compounds | mg/kg p.o. | % inhibition vs. controls | statistical significance vs. controls (Dunnet's test) |
|---|---|---|---|
| Ambroxol | 100 | 34.2 | >0.05 |
| Fominoben | 50 | 63.4 | <0.01 |
| YS-912 | 50 | 61.0 | <0.01 |
| Codeina fosfato | 5 | 56.1 | <0.01 |

The above data evidence the high activity of YS 912 compared with other well-known antitussive agents.

On the other hand, Ambroxol turns out to be poorly effective, lacking any statistical significance, even at doses twice than those used for YS 912.

3. Cough induced by mechanical stimulation in dog.

The procedure described by J. G. Widdicombe in "Evaluation of drug activities; pharmacometrics"-Academic Press-New York 1964-Vol. 2 Chapt. 24 Page 523, was used, comparing YS 912 with Ambroxol, Fominoben and Codeine phosphate.

The results are reported in table 3 hereinbelow.

| Compounds | mg/kg p.o. | % inhibition vs. controls | statistical significance vs. controls (Dunnet's test) |
|---|---|---|---|
| Ambroxol | 100 | 13.5 | N.S. |
| Fominben | 50 | 59.0 | <0.01 |
| YS-912 | 50 | 54.0 | <0.01 |
| Codeina fosfato | 5 | 63.1 | <0.01 |

In this test also the antitussive activity of YS 912 is confirmed, which turns out to be comparable to that of the two control compounds used at pharmacological standard doses. Ambroxol, used at doses twice those of YS 912, displayed substantially no effectiveness, accordingly with no statistical significance.

BRONCHOSECRETOLYTIC ACTIVITY

The procedure described by H. Mawatari (Kagoshima Daigaku Igaku Zasshi 27, 561; 1976) modified by G. Graziani and P. Cazzulani-(Il Farmaco Ed. Pr. 36, 167; 1981) was used, comparing YS 912 with Ambroxol at the same weight doses.

The obtained results are reported in the following Table 4. Values are for means of 12 animals.

| Compounds | Dose mg/kg p.o. | Fluorescein amount in bronchial fluid | % v.s. controls | Statistical significance (Dunnet's test) |
|---|---|---|---|---|
| Controls | = | 0.26 ± 0.03 | = | = |
| YS-912 | 12.5 | 0.31 ± 0.03 | 19.23 | P > 0.05 |
|  | 25.0 | 0.34 ± 0.04 | 30.76 | P > 0.05 |
|  | 50.0 | 0.38 ± 0.04 | 46.15 | P > 0.05 |
| Ambroxol | 12.5 | 0.32 ± 0.03 | 23.07 | P > 0.05 |
|  | 25.0 | 0.33 ± 0.02 | 26.92 | P > 0.05 |
|  | 50.0 | 0.37 ± 0.03 | 42.30 | P > 0.05 |

The calculated effective doses 50 were as follows:

| $DE_{50}$: | Ambroxol | = 95.19 mg/kg |
|---|---|---|
|  | MR-912 | = 60.04 mg/kg |

In this test both compounds proved to have an high effectiveness, YS 912 being anyway more favourable.

PHARMACOKINETICS

Acute study in the animal.

A study was carried out on the rat, by comparing the kinetic profiles of YS 912 and Ambroxol, after single administration at equimolecular doses.

The analysis of the results from the two different groups evidenced that:

in the animals treated with Ambroxol, the plasmatic concentration peak takes place at about the second hour, then it gradually decreases and it can be dosed even at the 12th hour;

in the animals treated with YS 912, the compound adsorption is fast and high, the peak being recorded after 30 minutes; integer YS 912 is found at still appreciable concentrations at the 6th hour, then being metabolized according to a slower kinetic, the main metabolite being Ambroxol;

the plasmatic half-life of YS 912 is higher by 30% than that of Ambroxol, this higher value being evidenced also in the case of the AUC.

"In steady" study in the animal.

After administration to the rat of equimolecular doses of YS 912 and Ambroxol during 6 days, by means of the calculation of pharmacokinetic constants, it could be possible extrapolate that, in human clinic, two daily administrations of YS 912 allow to achieve plasmatic concentrations (and therefore therapeutical effectiveness) which can be compared with those obtained after three daily administrations of Ambroxol.

I claim:

1. 2-Benzoylamino-3,5-dibromo-N-(4-hydroxycyclohexyl)benzylamine of formula (I)

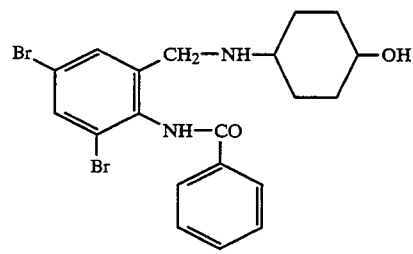

and pharmaceutically acceptable acid addition salts.

2. 2-Benzoylamino-3,5-dibromo-N-(4-hydroxycyclohexyl)benzylamine hydrochloride.

3. A pharmaceutical composition having antitussive and mucus regulating activity in unit dosage form, containing a compound according to claim 1 in the amount of 5–100 mgs as the active ingredient.

4. A method of treatment of a living subject affected by cough or mucus or both cough and mucus which consists of administering to said subject an effective amount of the compound of formula 2-Benzoylamino-3,5-dibromo-N-(4-hydroxycyclohexyl) benzylamine of formula (I)

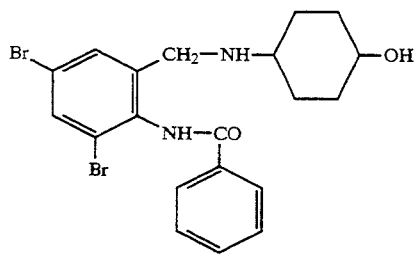
or a pharmaceutically acceptable acid addition salt thereof.
* * * * *
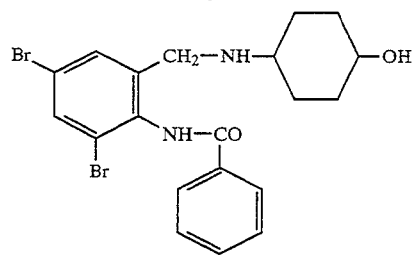
or a pharmaceutically acceptable acid addition salt thereof.
* * * * *